(12) United States Patent
Oyler

(10) Patent No.: US 8,475,543 B2
(45) Date of Patent: *Jul. 2, 2013

(54) TWO-STAGE PROCESS FOR PRODUCING OIL FROM MICROALGAE

(75) Inventor: James R. Oyler, Salt Lake City, UT (US)

(73) Assignee: Genifuel Corporation, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 13/026,767

(22) Filed: Feb. 14, 2011

(65) Prior Publication Data

US 2011/0131869 A1    Jun. 9, 2011

Related U.S. Application Data

(63) Continuation of application No. 11/966,917, filed on Dec. 28, 2007, now Pat. No. 7,905,930.

(60) Provisional application No. 60/877,786, filed on Dec. 29, 2006.

(51) Int. Cl.
| | | |
|---|---|---|
| *C10L 1/18* | (2006.01) | |
| *A01H 13/00* | (2006.01) | |
| *C12P 7/06* | (2006.01) | |
| *C12P 5/00* | (2006.01) | |
| *C12N 1/12* | (2006.01) | |
| *C12M 3/00* | (2006.01) | |

(52) U.S. Cl.
USPC ............... 44/388; 47/1.4; 435/134; 435/161; 435/166; 435/257.1; 435/257.6; 435/292.1

(58) Field of Classification Search
USPC .............. 44/388; 47/1.4; 435/134, 257.1, 435/257.6
See application file for complete search history.

(56) References Cited

U.S. PATENT DOCUMENTS

| | | | |
|---|---|---|---|
| 2,383,579 | A | 8/1945 | Allen et al. |
| 2,383,632 | A | 8/1945 | Trent |
| 3,958,364 | A | 5/1976 | Schenck et al. |
| 4,341,038 | A | 7/1982 | Bloch et al. |
| 4,472,503 | A | 9/1984 | Matsuo et al. |
| 4,743,545 | A | 5/1988 | Torobin |
| 5,316,927 | A | 5/1994 | Zaks et al. |
| 5,417,824 | A | 5/1995 | Greenbaum |
| 5,578,472 | A | 11/1996 | Ueda et al. |
| 5,776,344 | A | 7/1998 | McCarty et al. |
| 5,788,841 | A | 8/1998 | Dickerson |
| 6,237,284 | B1 | 5/2001 | Erickson |
| 6,326,470 | B1 | 12/2001 | Cosgrove |
| 6,790,669 | B1 | 9/2004 | Pfeiffer |
| 7,112,229 | B2 | 9/2006 | Khalil et al. |
| 7,135,308 | B1 | 11/2006 | Bush et al. |
| 7,252,165 | B1 | 8/2007 | Gruenwald et al. |
| 7,905,930 | B2 | 3/2011 | Oyler et al. |
| 7,977,076 | B2 | 7/2011 | Oyler et al. |
| 2002/0072109 | A1 | 6/2002 | Bayless et al. |
| 2002/0185557 | A1 | 12/2002 | Sparks |
| 2005/0112735 | A1 | 5/2005 | Zappe et al. |
| 2005/0210739 | A1 | 9/2005 | Esen et al. |
| 2005/0234278 | A1 | 10/2005 | Van Egmond et al. |
| 2006/0094089 | A1 | 5/2006 | Barclay |
| 2006/0186020 | A1 | 8/2006 | Gomes |
| 2006/0286205 | A1 | 12/2006 | Fichtali et al. |
| 2007/0048859 | A1 | 3/2007 | Sears |
| 2007/0260102 | A1 | 11/2007 | Duarte Santiago et al. |
| 2007/0292929 | A1 | 12/2007 | Weiner et al. |
| 2008/0160593 | A1 | 7/2008 | Oyler |
| 2009/0077863 | A1 | 3/2009 | Oyler |
| 2009/0269839 | A1 | 10/2009 | Oyler et al. |
| 2010/0304452 | A1 | 12/2010 | Oyler et al. |
| 2011/0136189 | A1 | 6/2011 | Oyler et al. |

FOREIGN PATENT DOCUMENTS

| | | |
|---|---|---|
| WO | WO 2006/121761 | 11/2006 |
| WO | WO 2007/013899 | 2/2007 |
| WO | WO 2007/081545 | 7/2007 |
| WO | WO 2008/008262 | 1/2008 |
| WO | WO 2008/083352 | 7/2008 |

OTHER PUBLICATIONS

U.S. Appl. No. 12/790,588, filed May 28, 2010; James R. Oyler; office action issued Aug. 8, 2011.
Algae Oil Extraction; From Oilgae.com—Oil and Biodiesel from Algae; www.oilgae.com/algae/oil/extract/extract.html; pp. 1-4; as accessed on Nov. 27, 2006.
Barrionuevo; Archer Daniels to Look Beyond Corn for Fuel Sources; New York Times; Nov. 9, 2005; www.nytimes.com/2006/11/09/Business/09adm.html?ei=5088&en=0e5de3501bbb3.
Brigs; Widescale Biodiesel Production from Algae; University of New Hampshire, Physics Dept.; UNH Biodiesel Group; Revised Aug. 2004; www.unh.edu/p2biodiesel/article_alge.html; pp. 1-11.
Erickson; Cellulosic Ethanol and Biorefineries: The Future is Now, Powerpoint; accessed Mar. 28, 2008; http://www.bio.org/ind/biofuel/EthanolfromCelluloseFutureisNew.pdf.
Gerpen et al.; Biodiesel Production Technology; Aug. 2002-Jan. 2004; NREL/SR-510-36244; Chpt 8; pp. 56-65; http://www.nrel.gov/docs/fy04osti36244.pdf.
Grepen et al; Biodiesel Production Technology, Subcontractor Report; National Renewable Energy Laboratory/US Dept. of Energy; Office of Energy Efficiency and Renewable Energy; Contract No. DE-AC36-99GO10337, NREL/SR-510-36244; Jul. 2004; pp. 1-106.
Greenfuel Technologies Corporation: Emissions to Biofuels Technology; www.greenfuelonlin.com/technology.htm; pp. 10-12 as accessed on Nov. 27, 2006.

(Continued)

*Primary Examiner* — Herbert J Lilling
(74) *Attorney, Agent, or Firm* — Thorpe North & Western LLP

(57) ABSTRACT

A process for production of biofuels from algae can include cultivating an oil-producing algae by promoting sequential photoautotrophic and heterotrophic growth. The method can further include producing oil by heterotrophic growth of algae wherein the heterotrophic algae growth is achieved by introducing a sugar feed to the oil-producing algae. An algal oil can be extracted from the oil-producing algae, and can be converted to form biodiesel.

14 Claims, 1 Drawing Sheet

OTHER PUBLICATIONS

Korus et al; Transesterification Process to Manufacture Ethyl Ester on Rape Oil; White Paper; Accessed Mar. 28, 2008; http://journeytoforever.org/biofueld_library/EthylEsteroRapeOil.pdf.

Oilagae.com—Oil from Algae! Biodiesel from Algae Oil—Info; Resources; News and Links; www.oilgae.com; pp. 1-4; as accessed on Nov. 27, 2006.

Overend; Hydrogen from Algae; Nationalk Renewable Energy Laboratory; ASES—Renewable Hydrogen Forum; Apr. 10-11, 2003; World Resources Institute; Washing tond, DC.

Peterson et al; Toxicology; Biodegradablity and Environmental Benefits of Biodiesel; Whte Paper; Accessed Mar. 28, 2008; http://www.biodiesel.org/resources/reportsdatabase/reports/mar/19940101_mac-002.pdf.

Related Case: U.S. Appl. No. 13/026,774, filed Feb. 14, 2011; James R. Oyler.

Related Case: U.S. Appl. No. 13/026,767, filed Feb. 14, 2011; James R. Oyler.

Schubert; Can Biofuels Finally Take Center Stage?; Nature Biotechnology Jul. 7, 2006; vol. 24 No. 7; pp. 777-784; www.nature.com/naturebiotechnology.

Sheehan et al; A Look Back at the US Department of Energy's Aquatic Species Program—biodisel from Algae, Close-Out Report; National Renewable Energy Laboratory/US Department of Energy; NREL/TP-580-24190; Jul. 1998.

Ulf Schuchardt et al.; Transesterification of Vegetable Oils: a Review; J. Braz. Chem. Soc.; 1998; vol. 9, No. 1; pp. 199-210.

Xiaoling Miao et al.; Biodiesel Production from Heterotrophic Microalgal Oil; Department odf Biological Sciences and Biotechnology; Tsinghua University, Beiging 100084, PR China; Biosource Technology 97; 2006; pp. 841-846.

U.S. Appl. No. 13/291,321, filed Nov. 8, 2011; James R. Oyler; office action dated Sep. 27, 2012.

U.S. Appl. No. 11/966,898, filed Dec. 28, 2007; James R. Oyler; notice of allowance dated Nov. 21, 2012.

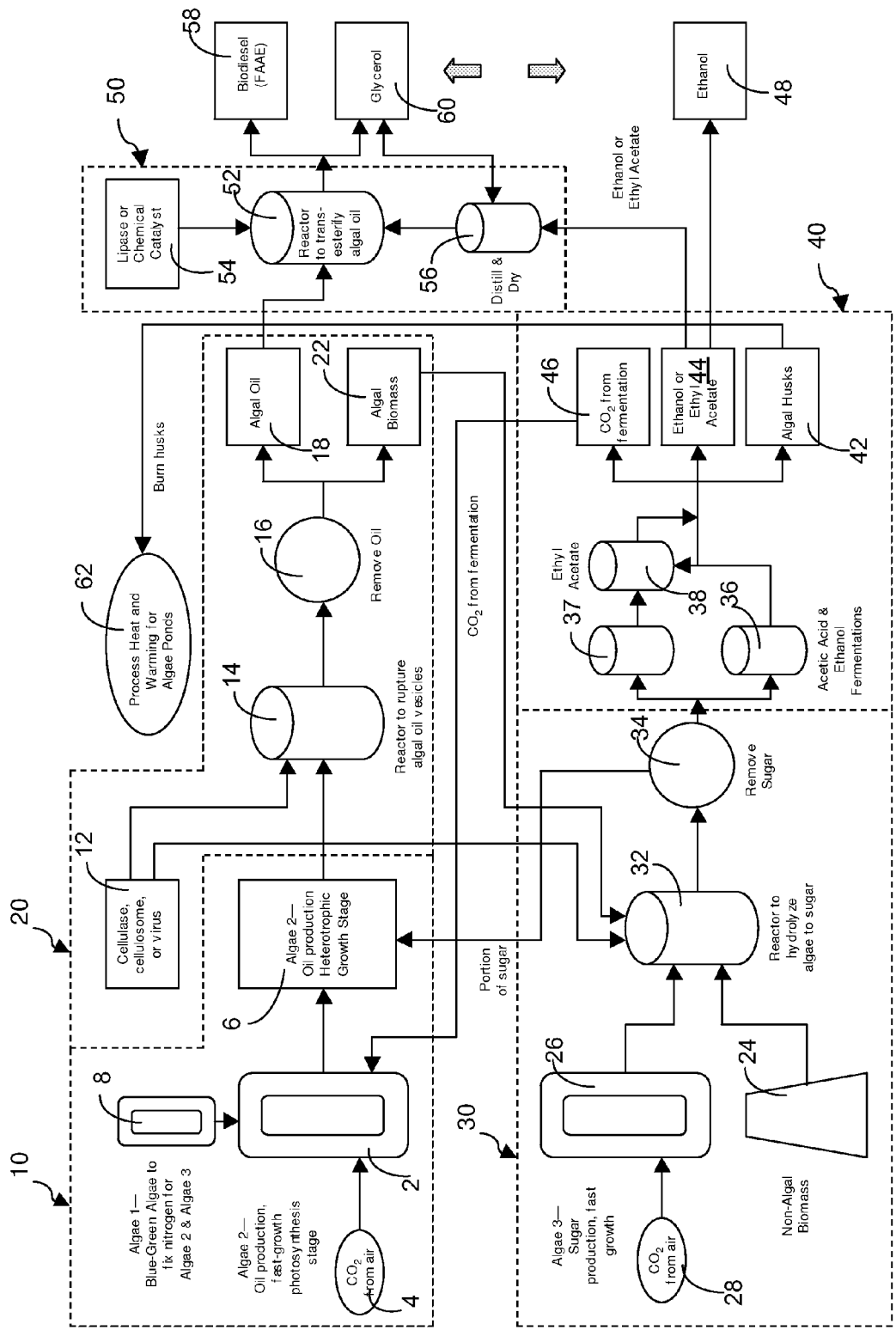

TWO-STAGE PROCESS FOR PRODUCING OIL FROM MICROALGAE

RELATED APPLICATIONS

This application is a continuation of U.S. patent application Ser. No. 11/966,917 filed on Dec. 28, 2007, now U.S. Pat. No. 7,905,930 which claims the benefit of U.S. Provisional Patent Application No. 60/877,786, filed on Dec. 29, 2006, both of which are incorporated herein by reference.

FIELD OF THE INVENTION

The present invention relates generally to conversion of algae and other biomass to biofuels such as biodiesel or bioethanol. Accordingly, the present invention involves the fields of chemistry, biochemistry, genetic engineering, process engineering, algaculture, biofuels, mechanical engineering, and thermodynamics.

BACKGROUND OF THE INVENTION

Increased market prices for energy and fuels are driven by a number of factors including a depletion of easily accessible petroleum and natural gas deposits, growth of emerging economies, and mounting environmental concerns. Consequently, these increasing energy prices will eventually require a significant restructuring and/or replacement of a major portion of fossil fuels by renewable energy technologies such as biomass-based fuels.

Approximately 67% of the petroleum used in the United States is currently used in transportation. While the transportation sector accounts for less than 30% of total U.S. energy use, it is by far the largest user of petroleum products, since electricity production and industrial processes (the other major energy-using sectors) rely mostly on coal, natural gas, nuclear, or hydroelectric energy. Most of the remaining energy use is residential, which is a mix of all the foregoing forms. Of the petroleum used, over 50% is now imported from outside the U.S. Petroleum imports are of increasing concern because of price escalation and the large proportion of imports coming from potentially unreliable sources. In addition, concerns are growing that "greenhouse gases" released from fossil fuels may contribute to climate changes. For economic, environmental, and political reasons, therefore, it is highly desirable to reduce the amount of petroleum burned, which practically means that an alternative fuel must be provided for the transportation fleet, in addition to changes in the fleet composition.

Much research has been devoted to a long-term future in which the transportation fleet is powered by hydrogen—the "hydrogen economy." However, this goal has proven elusive and does not appear practical in the foreseeable future. Instead, a more likely path to reducing or replacing petroleum in transportation is the use of biofuels. Biofuels are so named because they are produced from biological sources, primarily plant growth. Petroleum products were also once produced by biological processes, with the plant or animal products from many millions of years ago accumulating in fossil forms of hydrocarbons. Almost all biological energy starts with the conversion of sunlight to carbohydrates through photosynthesis. In essence, the use of petroleum releases the energy of sunlight stored in the past, while biofuel production utilizes energy captured from the sun on a current basis.

In its simplest form, photosynthesis uses energy from the sun to convert carbon dioxide and water from the environment into carbohydrates. It is possible to release energy directly from some forms of these carbohydrates (e.g. burning wood or straw), but for modern transportation such forms are not practical. Instead, a more practical fuel can be produced by processing the plant carbohydrates into liquid forms giving higher energy densities and combustion processes more acceptable to internal combustion engines—in other words, biofuels.

The use of biofuels generally is by no means a new or novel idea. In fact, some of the earliest internal combustion engines ran on biofuels. When Rudolf Diesel developed the diesel engine, the fuel he used was peanut oil. Henry Ford was committed to the use of ethanol in his cars, and one of the best-known early trademarks for fuel stations in the US was "Ethyl." Both peanut oil and ethanol were, of course, displaced by petroleum-based products including diesel fuel and gasoline as those products became abundant and cheap. Because of the economic, environmental, and political factors mentioned above, however, the advantage of petroleum is now disappearing and biofuels are once again becoming a top candidate fuel for vehicles.

Many analyses have been done of the true economics of biofuel production compared to petroleum-based fuels, and most of these studies show that in the absence of government subsidies current forms of biofuels are somewhat more expensive on an equivalent-energy basis than petroleum fuels. However, the cost curves have been converging and are likely to cross within the next few years with the development of improved biofuel production processes.

Economically, if future carbon credits are included in the analysis, then biofuels may be cheaper than petroleum fuels even today and certainly cheaper in the future. Environmentally, the process of creating and releasing energy from biofuels should be substantially carbon-neutral, since carbon from the atmosphere is stored in the fuel, then released once again when burned. With today's biofuel production, this ideal statement is not true, since petroleum fuels are used in the production of biofuels (primarily through agriculture). Nevertheless, as production processes for biofuels improve it will be possible to achieve much closer to carbon-neutrality and at lower cost than fossil fuels.

Engines for Transportation

The current transportation fleet uses mostly internal combustion engines operating either as compression ignition (diesel) engines burning diesel fuel or spark ignition engines burning gasoline. A much smaller amount of fuel is used in jet or turbine engines burning jet fuel (similar to kerosene). In the U.S., the ratio of gasoline to diesel fuel is about two to one, with 120 billion gallons of gasoline and 60 billion gallons of diesel fuel used annually. About 20 billion gallons of other fuels are used, giving a total of approximately 200 billion gallons used annually in transportation.

Diesel engines are 30 to 40% more efficient than gasoline engines, meaning that thermodynamically diesel engines extract 30 to 40% more usable energy from the input fuel. This is true because diesel engines operate at higher pressures (higher compression) and higher combustion temperatures than gasoline engines. If all gasoline engines were replaced with diesel engines the amount of fuel needed in total would be reduced from 200 billion gallons to approximately 160 billion gallons by this step alone.

This is a practical step to reduce petroleum use which uses currently available technologies, and will therefore likely occur worldwide. The process is already well advanced in Europe and Japan. In Europe, more than 50% of the new passenger fleet is diesel, compared with a much lower percentage in the U.S. In the U.S., passenger car drivers have traditionally avoided diesels for a number of reasons, and some states, notably California, have created regulations which make diesels unattractive, in order to reduce emissions associated with diesel engines, including soot, nitrogen oxides, sulfur and "diesel smell." In addition, most drivers consider diesels to be noisy, rough, heavy, less powerful, and more expensive than gasoline engines.

To some extent these complaints have been true, but new technology is solving many of these problems. The most prominent new diesel technology is the growing use of common-rail fuel systems, which provide higher pressure and more uniform injection of fuel into the engine. This results in cleaner combustion, more power, less noise, and smoother operation. Ultra-low-sulfur fuels are also being introduced, which will remove most sulfur emissions. Nitrogen oxides will be substantially reduced in new engines in the next few years by improved catalytic converters. Further, as will be discussed below, biodiesel burns cleaner and with lower emissions than even the most advanced petroleum-based diesel fuels, further tilting the balance toward diesel engines.

With these and other developing technologies a very attractive diesel-electric vehicle with excellent driving characteristics (superior to most vehicles today) could replace current propulsion technologies, while providing much higher operating efficiencies. The efficiencies could double the mileage of current gasoline-engine vehicles while not sacrificing power, comfort, acceleration, or drivability.

Even if these changes in the transportation fleet do not take place, diesel fuel will still be required in very large quantities for the foreseeable future. In addition, the production process for biodiesel is generally more efficient than the production process associated with bioethanol or other alcohols, which is the other main alternative biofuel. Based on this analysis, the most desirable fuel for the future is diesel fuel, and emphasis should be placed on biodiesel production.

Current Biofuel Sources

By far the largest volume of biofuel used today is in the form of bioethanol for spark-ignition engines, with a smaller amount in the form of biodiesel for compression-ignition engines. World production of bioethanol and biodiesel is shown in Table 1.

TABLE 1

Primary World Production of BioFuels in 2004

| Biofuel Type | Production by Region | Feedstock | Volume |
| --- | --- | --- | --- |
| Bioethanol | Brazil | Sugarcane | 5 billion gallons |
|  | USA | Corn | 4 billion gallons |
|  | EU | Sugarbeet | 1 billion gallons |
| Biodiesel | Germany | Rapeseed | 600 million gallons |
|  | USA | Soybeans | 50 million gallons |

Both bioethanol and biodiesel are produced primarily from plants. The plant material used for ethanol is a form of sugar in Brazil and the EU, and corn in the U.S. For biodiesel, the primary source is oil from rapeseed in Germany or soybeans in the U.S. The reason why these sources are used is that they are well known and already grown, and because the sugar, starch, or oil is relatively easy to extract and process into fuel.

However, in the long term using food crops for fuel is not optimal. Food crops require premium land, abundant water, and large inputs of energy in the form of agricultural machinery and fertilizer. In addition, sugar in Brazil is often grown on land which might otherwise be rainforest, thus further depleting an already diminishing environmental resource. Competition for food inputs will only increase, and in the event of food shortages, fuel for vehicles would become expensive. Moreover, fuel yields of these crops are low enough that unrealistic amounts of land would be needed to significantly or completely replace fossil fuels.

SUMMARY OF THE INVENTION

The present invention, as disclosed herein, addresses the above-described problems in novel ways by using algae to produce lipids (oil) which can be readily converted into biodiesel.

In accordance with one aspect, a process for production of biofuels from algae can include cultivating an oil-producing algae by promoting sequential photoautotrophic and heterotrophic growth. The method can further include producing oil by heterotrophic growth of algae wherein the heterotrophic algae growth is achieved by introducing a sugar feed to the oil-producing algae. An algal oil can be extracted from the oil-producing algae, and can be converted to form biodiesel.

In another aspect, a system for production of biodiesel from algae can include a feed biomass source, algae growth reservoirs, a sugar separator, an oil extraction bioreactor, and a conversion reactor.

Additional features and advantages of the invention will be apparent from the following detailed description which illustrates, by way of example, features of the invention.

BRIEF DESCRIPTION OF THE DRAWING

Aspects of the invention can be better understood with reference to the following drawing.

FIG. 1 is a process flow diagram of a system for production of biofuels from algae in accordance with an embodiment of the present invention.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a step" includes reference to one or more of such steps.

As used herein, "reaction" is intended to cover single step and multi-step reactions which can be direct reactions of reactants to products or may include one or more intermediate species which can be either stable or transient.

As used herein, "biofuels" refers to any fuel, fuel additive, aromatic, and/or aliphatic compound derived from a biomass starting material such as algae, corn, switchgrass, or the like.

As used herein, "biologically rupturing" refers to any process which uses a biological agent to damage algae cell walls and/or oil vesicle walls which results in a degradation, destruction or loss of integrity to such walls sufficient to allow oil materials to flow therefrom. Biological agents can be any biochemical material which has the desired effect such as, but not limited to, enzymes, viruses, or the like.

As used herein, "transesterify," "transesterifying," and "transesterification" refer to a process of exchanging an alkoxy group of an ester by another alcohol and more specifically, of converting algal oil, e.g. triglycerides, to biodiesel, e.g. fatty acid alkyl esters, and glycerol. Transesterification can be accomplished by using traditional chemical processes such as acid or base catalyzed reactions, or by using enzyme-catalyzed reactions.

As used herein, "substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no deleterious effect on the composition.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of about 1% to about 20% should be interpreted to include not only the explicitly recited concentration limits of 1% to about 20%, but also to include individual concentrations such as 2%, 3%, 4%, and sub-ranges such as 5% to 15%, 10% to 20%, etc.

Generally, in accordance with the present invention, a process for production of biofuels from algae can include cultivating an oil-producing algae by promoting both autotrophic and heterotrophic growth. Heterotrophic growth can include introducing an algal feed to the oil-producing algae to increase the formation of algal oil. The algal oil can be extracted from the oil-producing algae using biological agents and/or other methods such as mechanical pressing. The resulting algal oil can be subjected to a transesterification process to form biodiesel.

Biomass as a Biofuel Source

Rather than using high-value food crops to produce fuel, an alternative is to use fast-growing plants that can grow on less valuable land than food crops, and require less input such as water, fertilizer, and pesticides compared to food crops. Since these plants do not produce the high-value starch and sugar of food crops, they may not be as easy to use or convert into fuels. Instead, processes can be developed which convert the lignocellulose or other mass of the plants into a precursor (such as starch or sugar) which can be used for fuel production.

The conversion of cellulose or other biomass into starch or sugar is more difficult than the conversion of starch or sugar into fuel. The conversion can be done with heat and chemicals, e.g. essentially cooking the material to break it down, but large amounts of energy are required, which is usually supplied from fossil fuels. The cost of this step makes the final biofuel more expensive, and also reduces the net gain in energy because of the fuels which must be burned in the cooking stage, and also because the starch or sugar degrades somewhat in the cooking process and yields less energy.

Recently, biotechnology has been employed to find biological pathways to break down biomass into sugars or other bioavailable materials, which can then be fermented into alcohol or used as food for further biological growth. In general such biological processes use enzymes (biological catalysts), some of which have been identified and can be produced on an industrial scale. Such enzymes are known as cellulases. In addition, more efficient catalysts have been identified, in which a series of enzymes is arrayed in a sequence to break down the cellulose more rapidly and efficiently. These structured arrays are known as cellulosomes, and can be produced by certain bacteria or fungi.

With the problem of converting cellulosic mass into bioavailable feed becoming better understood, the challenge is to produce sufficient biomass to produce the quantity of fuels needed. A common starting point is to begin with the food crops already used for biofuels and use the plant more efficiently. Specifically, parts of the plant other than just the sugar or starch can be used. In the case of corn, the remainder of the plant other than the ears of corn is known as corn stover. In the case of sugarcane, it is known as bagasse. By recovering and using stover and bagasse, additional fuel can be produced from the same land. Straw from other food crops such as wheat or rice can be used in the same way. However, even this combination of materials is not close to enough to replace the volume of fossil fuels used in transportation.

Additional plants which might be used directly or indirectly to produce fuels include switchgrass, miscanthus, and certain fast-growing trees such as hybrid willows and poplars. Switchgrass is native to North America and can grow to ten feet tall, is perennial, grows in almost every state, even in marginal soils, and requires little water or fertilizer. It is likely that yields of switchgrass can be improved as further knowledge of the species is gained. However, using current yields of switchgrass, approximately 300 million acres would be needed to displace the current use of petroleum fuels for transportation. As a reference, the total land area of the lower 48 states of the U.S. is slightly less than 3 billion acres, and approximately 1 billion acres are used for crop production or rangeland for grazing, split nearly 50/50. Therefore, growing enough switchgrass would require approximately a 60% increase in crop area. While possible, this seems impractical.

Additionally, with current processes, the biomass yields ethanol as the output fuel. While certainly useable as a fuel, ethanol is far from ideal. Its energy content on a volume basis is about 30% less than the fossil fuels now used, and is not practical in current diesel engines. Ethanol also attracts water, which makes storage and handling critical to avoid exposure to water. The production process for ethanol is also not ideal, since energy is lost in the fermentation process. It is possible to form alcohols other than ethanol (e.g. butanol) from biomass, which can remove some of the disadvantages of ethanol, but the disadvantages of the fermentation process remain. In short, replacement of petroleum fuels in transportation will need other or additional fuels besides alcohols.

Algae as a Biofuel Source

A search for a biosource which would require less land area than grasses or other biomass leads back to one of the first photosynthetic organisms to evolve on earth—algae. Algae can produce 10 to 100 times as much mass as terrestrial plants in a year. In addition to being a prolific organism, algae is also capable of producing oils and starches that can be converted into biofuels.

The specific algae most useful for biofuel production are known as microalgae, consisting of small, often unicellular, types. These algae can grow almost anywhere. With more than 100,000 known species of diatoms (a type of algae), 40,000 known species of green plant-like algae, and smaller numbers of other algae species, algae will grow rapidly in nearly any environment, with almost any kind of water. Specifically, useful algae can be grown in marginal areas with limited or poor quality water, such as in the arid and mostly empty regions of the American Southwest. These areas also have abundant sunshine for photosynthesis. In short, algae can be an ideal organism for production of biofuels—efficient growth, needing no premium land or water, not competing with food crops, needing much smaller amounts of land than food crops, and storing energy in a desirable form.

Given the almost universal presence, ancient origins, importance, and versatility of algae, relatively little is actually known about systematic cultivation of this organism. One prominent source of modern information has been the U.S. National Renewable Energy Laboratory (NREL), which is part of the U.S. Department of Energy (DOE). NREL, located in Golden, Colo., is responsible for research and publication of information about renewable energy technologies and resources, including biofuel, solar and photovoltaic technology, fuel cells, hydrogen, geothermal, wind, and other energy sources.

Quoting from an NREL publication: "From 1978 to 1996, the U.S. Department of Energy's Office of Fuels Development funded a program to develop renewable transportation fuels from algae. A primary focus of the program, known as the Aquatic Species Program (or ASP) was the production of biodiesel from high lipid-content algae grown in ponds, utilizing waste $CO_2$ from coal fired power plants. During the almost two decades of this program, tremendous advances were made in the science of manipulating the metabolism of algae and the engineering of microalgae production systems."

Algae can store energy in its cell structure in the form of either oil or starch. Stored oil can be as much as 60% of the weight of the algae. Certain species which are highly prolific in oil or starch production have been identified, and growing conditions have been tested. Processes for extracting and converting these materials to fuels have also been developed but still leave much to be desired.

As described above, the primary source today for oil to produce biodiesel is the use of foodcrops such as rapeseed and soybeans. Neither of these is likely to be able to supply a significant percentage of the total fuel needed for the transportation fleet. Biomass such as grasses, residue from grain crops, woodland products or waste, and so forth can potentially supply a much larger amount of biofuels, but are almost all currently targeted toward the production of bioethanol. However, production of bioethanol is not optimum as a fuel source for reasons listed above.

In accordance with one aspect of the present invention, algae is grown, its energy stores are extracted and converted into useable fuels, and byproducts of the fuel production are either sold directly or fed back as inputs into algae growth and fuel production stages. This integrated system uses a minimum of external inputs other than sunlight, water, and carbon dioxide from the air.

Building on the NREL research, other approaches propose to locate algal growth facilities near power plants, which are major producers of carbon dioxide from combustion of fossil fuels. The otherwise wasted and potentially harmful carbon dioxide can be fed into algae growth reactors to increase growth, and in the process recapture carbon dioxide which would otherwise contribute to greenhouse gases. Despite some benefits of this plan, the amount of space available near power plants is limited and therefore the amount of biofuel that can be produced this way is similarly limited.

The present invention provides for the growth of algae photosynthetically. That is, the primary source of energy can be the sun and the atmosphere, not the burning of fossil fuels. In one detailed aspect, the processes of the present invention can include growing two sources of algae, which may or may not be different species. Each of these two sources of algae may in turn be accomplished in two stages—a light stage and a dark stage. In both stages, the algae can be grown in reservoir structures, such as ponds, troughs, or tubes, which are protected from the external environment and have controlled temperatures, atmospheres, and other conditions. Alternatively, if generic biomass is used as a feed source, it is anticipated that this can be purchased from growers of switchgrass or other biomass crop as described above. It is believed that the present invention is the most efficient of processes which utilize algae to form biofuels and will make a substantial contribution to the evolution from petroleum-based transportation fuels to biofuels.

A novel feature of the invention is the use of algae as an intermediary step which allows the production of biodiesel rather than bioethanol or other alcohol from generic biomass. In this aspect of the present invention, biomass can be depolymerized to produce sugar. The sugar is then fed to oil-producing algae, which convert the energy content of the sugar into oil (algal triglycerides), which can then be further converted into biodiesel. Most of the energy of the sugar ends up as useful fuel, rather than suffering the fermentation losses which occur during the production of alcohol, e.g. in the form of heat and carbon dioxide emissions.

Algal Growth Stage

In accordance with the present invention, algae growth reservoirs can include a carbon dioxide source and a circulating mechanism configured to circulate an oil-producing algae within the algae growth reservoirs. It was shown earlier that approximately 300 million acres of conventional biomass growth would be needed to totally displace today's transportation fuels. In contrast, less than 10 million acres of algae growth reservoirs would be needed. One way to achieve such large surface growth areas is in large ponds or in a captive marine environment. In one embodiment, a raceway pond can be used as an algae growth reservoir in which the algae is grown in shallow circulating ponds with constant movement around the raceway and constant extraction or skimming off of mature algae.

It is also known that certain species of algae are much more prolific in the production of oil or starch than others. Unfortunately, these species seem generally to be susceptible to predation or displacement by native or volunteer species which exist naturally in the environment where the growth reservoir is located. Moreover, in most locations, temperatures, while generally moderate, may reach extremes of heat or cold which could damage or at least retard the growth of the algae. For these and other reasons, some form of protection is usually desirable for the chosen algae species. In another aspect, low-cost greenhouses can be built over the raceway ponds. These greenhouses can have enough integrity to maintain a positive pressure with airlocks, filtration, and temperature control. This integrity can prevent the entrance of wild algae and can maintain desired conditions for the algae crop.

Some species of algae important for fuel production can grow in either light or dark conditions. In light conditions, growth is photoautotrophic (or simply autotrophic), meaning that light, e.g. sunlight, provides the energy needed for growth. In dark conditions, growth is heterotrophic, meaning that an outside form of energy or food other than light is needed. Autotrophic growth and heterotrophic growth are different growth mechanisms, and can be used in various ways in the two stages of the present invention to yield optimum fuel production.

Referring now to FIG. 1, an oil-producing algae can be cultivated in a cultivation sub-system 10. Both autotrophic and heterotrophic growth can be used to produce a useful quantity of algae and for the algae to produce useful oil. In one alternative embodiment of the present invention, the autotrophic growth and heterotrophic growth can be sequentially performed in a two-stage process. In the first stage 2, the algae can be grown in a greenhouse environment such as the raceway ponds as described above, although other growth environments may also be suitable. Non-limiting examples of growth environments or reservoirs which can be used include bioreactors, open ponds having various shapes and configurations, and the like. Each of these options can have benefits and drawbacks. For example, current bioreactors are prohibitively expensive for large scale production, although future developments may make this mechanism more attractive for use in connection with the present invention. In this first stage, the algae grows photosynthetically, with air circulation 4 providing the carbon source from atmospheric carbon dioxide with optional additional carbon dioxide from other intra or extra-process sources, e.g. fermentation or off-gas sequestration. The purpose of the light stage is to grow a large mass of green algae as quickly and cheaply as possible. This first-stage algae can then be skimmed off, moved, and/or exposed immediately to the second stage 6, or dark stage.

The structure of the dark or autotrophic stage 6 can be very similar to the light stage 2, except that the structure can be opaque rather than transparent to light as in the greenhouse, thus providing nearly dark conditions for growth. The opaque conditions can be provided by a movable covering, by a separate enclosure, or through any other suitable mechanism. In the dark stage certain conditions and nutrients can be optimized to encourage the production of starch or oil for conversion to fuels. For example, the nitrogen content of the water may be reduced, and food in the form of carbon dioxide and/or sugar can be fed into the water in a raceway pond. Certain nutrients, especially a balanced mix of magnesium and potassium, can be added to the algal food supply. Optionally, genetic manipulations of key metabolic factors in the algae to increase oil or starch production may be undertaken, or biological materials may be added to trigger or accelerate oil production. Similarly, the heterotrophic stage can be entirely or at least partially triggered by using a stress induction mechanism in order to shift growth from autotrophic to heterotrophic growth. Non-limiting examples of suitable stress induction mechanism can include light deprivation, nutrient deprivation (e.g. nitrogen and/or phosphorous), injection of a reactive oxygen source (e.g. ozone or peroxide), and/or chemical additives.

These steps can be taken to provide the optimal conditions to induce the algae to stop producing green mass and, instead, biologically convert to filling the cell bodies with as much oil or starch as possible. This effect has been conclusively demonstrated, and the underlying theory is that the dark condition and altered nutrient availability create stress in the algae, and in preparation for possible long-term harsh conditions the algae store up energy in the compact form of a lipid or starch by extracting carbon and energy from the available nutrients in lieu of green growth through photosynthesis.

This two-step sequence optimizes total production of the desired substances by first creating as many cell bodies as possible to increase the overall algae population, then altering the conditions to reduce creation of new cell bodies and instead fill them with oil or starch. Neither step alone would produce the desired effect useful for the present invention.

Generally, the oil growth reservoirs can include an algae growth control means for achieving both autotrophic growth and heterotrophic growth. The algae growth control means can include a stress induction mechanism for controlling available light and nutrient levels to the algae growth reservoir. An alternative embodiment can further include the addition of materials, which will initiate and induce the production of oils or starches directly. For example, a single algae growth reservoir can be subjected to a controllable light environment by retractable coverings, reversibly opaque coverings, or the like. Alternatively, the algae growth control means can include providing separate autotrophic growth reservoirs and heterotrophic growth reservoirs within the algae growth reservoirs which are operatively connected to one another and configured for autotrophic growth and heterotrophic growth, respectively.

Although a staged process can be used, a combined growth process can be preferred under some circumstances. For example, the autotrophic growth and heterotrophic growth can be performed substantially simultaneously or overlapping. In one detailed aspect of the present invention, the autotrophic growth and heterotrophic growth are performed substantially simultaneously by providing a lipid trigger to initiate and/or accelerate oil production during heterotrophic growth.

Strains of Algae

Lipid or oil-producing algae can include a wide variety of algae, although not all algae produce sufficient oil, as mentioned above. The most common oil-producing algae can generally include, or consist essentially of, the diatoms (bacillariophytes), green algae (chlorophytes), blue-green algae (cyanophytes), and golden-brown algae (chrysophytes). In addition a fifth group known as haptophytes may be used. Specific non-limiting examples of bacillariophytes capable of oil production include the genera *Amphipleura*, *Amphora*, *Chaetoceros*, *Cyclotella*, *Cymbella*, *Fragilaria*, *Hantzschia*, *Navicula*, *Nitzschia*, *Phaeodactylum*, and *Thalassiosira*. Specific non-limiting examples of chlorophytes capable of oil production include *Ankistrodesmus*, *Botryococcus*, *Chlorella*, *Chlorococcum*, *Dunaliella*, *Monoraphidium*, *Oocystis*, *Scenedesmus*, and *Tetraselmis*. In one aspect, the chlorophytes can be *Chlorella* or *Dunaliella*. Specific non-limiting examples of cyanophytes capable of oil production include *Oscillatoria* and *Synechococcus*. A specific example of chrysophytes capable of oil production includes *Boekelovia*. Specific non-limiting examples of haptophytes include *Isochrysis* and *Pleurochrysis*.

In one preferred aspect, the oil-producing algae can have oil content greater than about 20%, and preferably greater than about 30% by weight of the algae. Currently known strains contain a practical maximum oil content of about 40% by weight, although levels as high as 60% have been shown, and strains developed or discovered in the future may achieve practical maximums higher than 40%. Such strains would certainly be useful in connection with the present invention. In some embodiments, the oil production stage algae can comprises greater than 50% or consist essentially of the oil-producing algae. Optimal heterotrophic growth times can vary depending on the strain of algae and other operating parameters. This can involve a balance of oil production, feed costs, and diminishing returns of oil percentage increases. For example, algal strains which can reach 50% oil may take only 5 days to reach 35% and another 10 days to reach 50%. In such a case, it may be suitable to harvest the oil at five days and begin cultivating another batch rather than expending additional energy in growing the final 15% oil content. As a general guideline, heterotrophic growth times can range from 2 days to 2 weeks, and are often from about 4 to 7 days. At longer times, foreign algae, bacteria and other factors can make maintaining acceptable growth conditions progressively more difficult.

Further, the oil-producing algae of the present invention can include a combination of an effective amount of two or more strains in order to maximize benefits from each strain. As a practical matter, it can be difficult to achieve 100% purity of a single strain of algae or a combination of desired algae strains. However, when discussed herein, the oil-producing algae is intended to cover intentionally introduced strains of algae, while foreign strains are preferably minimized and kept below an amount which would detrimentally affect yields of desired oil-producing algae and algal oil. Undesirable algae strains can be controlled and/or eliminated using any number of techniques. For example, careful control of the growth environment can reduce introduction of foreign strains. Alternatively, or in addition to other techniques, a virus selectively chosen to specifically target only the foreign strains can be introduced into the growth reservoirs in an amount which is effective to reduce and/or eliminate the foreign strain. An appropriate virus can be readily identified using conventional techniques. For example, a sample of the foreign algae will most often include small amounts of a virus which targets the foreign algae. This virus can be isolated and grown in order to produce amounts which would effectively control or eliminate the foreign algae population among the more desirable oil-producing algae.

During autotrophic growth, nutrients can be supplied to the oil-producing algae. In one particular aspect, a nitrogen-fixing algae can be introduced to the oil-producing algae to supply nitrogen as a nutrient. The nitrogen-fixing algae (8 of FIG. 1) can be introduced by either mixing and/or additional process steps to release nitrogen for use by the oil-producing algae. In one embodiment, the nitrogen-fixing algae can include, or consist essentially of, cyanobacteria, i.e. blue-green algae. In another embodiment, the oil-producing algae may itself be cyanobacteria, which can then fix its own nitrogen, thereby reducing costs for the oil-producing growth.

Process to Select Strains of Algae for Optimal Growth and Oil Production

To achieve optimal oil production, three steps can be applied. The first is the selection of species of algae with desirable characteristics of growth, robustness, and high lipid production. The second is the identification of metabolic pathways involved in triggering and increasing lipid production, and the third is the application of mechanisms to affect these metabolic pathways.

Balance of Oil-Production Vs. Cellulose or Starch Production

While the process of the present invention can produce both biodiesel and bioethanol, it is optimized for the production of biodiesel. Biodiesel production is preferable for several reasons, the first of which is the higher efficiency and likely evolution of a diesel-based transportation fleet. The second reason is that the production of energy in the form of oil (lipids) by algae is more useful than the production of starch. If equal volumes of oil and starch are produced, the oil will contain significantly more energy. For example, the energy content in a typical algal lipid is 9 kcal/gram compared to 4.2 kcal/gram for typical algal starch. Third, in the production of sugars from starch, not all the starch is saccharified into sugars which can be easily fermented, so a portion may be lost as unused sugars. The final reason is that the production of biodiesel from the algal oil is essentially energy-neutral, so nearly all of the energy content of the algal oil is retained in the biodiesel. In contrast, the production of alcohol from biomass or starch is less efficient, especially during the fermentation stage which converts the sugars derived from the biomass or starch into alcohol. Fermentation is exothermic, with heat being generated that must be removed and often wasted. In addition, one half of the carbon in the sugar is released during fermentation as carbon dioxide and is therefore not available for fuel energy. For all of these reasons biodiesel production is more efficient overall than bioethanol production and therefore the goal of highest efficiency and lowest cost is served by maximizing biodiesel production.

Nevertheless, starch-producing or biomass producing algae are one important aspect of the present invention, as described below in more detail. For example, starch products or sugars converted from algal biomass can be used to produce feed for the oil-producing algae and/or production of ethanol or ethyl acetate for use in transesterification of algal oil. Such algal biomass can be the same or different algae strains than those used as the oil-producing algae. If the starch or biomass growth is greater than needed, the excess can be converted to ethanol and sold profitably as a second product in addition to biodiesel. Carbon dioxide released during fermentation can be fed back into the algal growth stage, substantially eliminating at least this form of energy loss in the fermentation process.

Recovery of Oil, Starch and Sugar from the Algae

Algae store oil inside the cell body, sometimes but not always in vesicles. This oil can be recovered in several relatively simple ways, including solvents, heat, and/or pressure. However, these methods typically recover only about 80% to 90% of the stored oil. The processes of the present invention offer more effective oil extraction methods which can recover close to 100% of the stored oil at low cost. These methods include or consist of depolymerizing, such as biologically breaking the walls of the algal cell and/or oil vesicles, if present, to release the oil from the oil-producing algae.

Oil can be extracted in extraction sub-system 20. The extraction sub-system can include an oil extraction bioreactor 14 operatively connected to the algae growth reservoirs 6, 2. Within the oil extraction bioreactor the cell walls and algal oil vesicles of the oil-producing algae can be biologically ruptured to yield an algal oil and algal residue. A biological agent source 12 can be operatively connected to the oil extraction bioreactor. The processes of the present invention can generally use at least one of three types of biological agents to release algae energy stores, i.e. enzymes such as cellulase or glycoproteinase, structured enzyme arrays or system such as a cellulosome, a viral agent, or a combination thereof. A cellulase is an enzyme that breaks down cellulose, especially in the wall structures, and a cellulosome is an array or sequence of enzymes or cellulases which is more effective and faster than a single enzyme or cellulase. In both cases, the enzymes break down the cell wall and/or oil vesicles and release oil or starch from the cell. Cellulases used for this purpose may be derived from fungi, bacteria, or yeast. Non-limiting examples of each include cellulase produced by fungus *Trichoderma reesei* and many genetic variations of this fungus, cellulase produced by bacteria genus *Cellulomonas*, and cellulase produced by yeast genus *Trichosporon*. A glycoproteinase provides the same function as a cellulase, but is more effective on the cell walls of microalgae, many of which have a structure more dependent on glycoproteins than cellulose.

In addition, a large number of viruses exist which invade and rupture algae cells, and can thereby release the contents of the cell—in particular stored oil or starch. Such viruses are an integral part of the algal ecosystem, and many of the viruses are specific to a single type of algae. Specific examples of such viruses include the *chlorella* virus PBCV-1 (Paramecium Bursaria *Chlorella* Virus) which is specific to certain *Chlorella* algae, and cyanophages such as SM-1, P-60, and AS-1 specific to the blue-green algae *Synechococcus*. The particular virus selected will depend on the particular species of algae to be used in the growth process. One aspect of the present invention is the use of such a virus to rupture the algae so that oil or starch contained inside the algae cell wall can be recovered. In another detailed aspect of the present invention, a mixture of biological agents can be used to rupture the algal cell wall and/or oil vesicles.

Mechanical crushing, for example, an expeller or press, a hexane or butane solvent recovery step, supercritical fluid extraction, or the like can also be useful in extracting the oil from oil vesicles of the oil-producing algae. Alternatively, mechanical approaches can be used in combination with biological agents in order to improve reaction rates and/or separation of materials. Regardless of the particular biological agent or agents chosen such can be introduced in amounts which are sufficient to serve as the primary mechanism by which algal oil is released from oil vesicles in the oil-producing algae, i.e. not a merely incidental presence of any of these.

Once the oil has been released from the algae it can be recovered or separated 16 from a slurry of algae debris material, e.g. cellular residue, oil, enzyme, by-products, etc. This can be done by sedimentation or centrifugation, with centrifugation generally being faster. Starch production can follow similar separation processes. Recovered algal oil 18 can be collected and directed to a conversion process 50 as described in more detail below. The algal biomass 22 left after the oil is separated may be fed into the depolymerization stage described below to recover any residual energy by conversion to sugars, and the remaining husks can be either burned for process heat 62 or sold as an animal food supplement or fish food.

Conversion of Starch and Cellulose to Sugar (Depolymerization or Saccharification)

An algal feed can be formed from a biomass feed source as well as an algal feed source. Biomass from either algal or terrestrial sources can be depolymerized in a variety of ways such as, but not limited to saccharification, hydrolysis or the like. The source material can be almost any sufficiently voluminous cellulose, lignocellulose, polysaccharide or carbohydrate, glycoprotein, or other material making up the cell wall of the source material. Suitable algal feed can be prepared in feed production sub-system 30. In one aspect of the present invention, the algal feed can be provided by cultivating algae 26, including supplying any nutrients 28, and extracting the algal feed therefrom after depolymerization. Alternatively, or in combination, the algal feed can be provided by cultivating a non-algal biomass 24 and extracting the algal feed therefrom. Algae can be cultivated on-site and other terrestrial biomass can transported from exterior sources or growers. Preferably, at least some of the biomass can be cultivated on-site in order to reduce transportation costs. Suitable non-algal biomass can include any starch or cellulosic material such as, but in no way limited to, corn, sugarcane, switchgrass, miscanthus, grasses, grains, grass residues, grain residues, poplar or willow trees, other trees, tree residues, biorefuse, mixtures of these materials, and the like.

In one embodiment of the invention, non-algal biomass can be the only input source for sugar production, and algae in the oil-production sub-system 10 essentially becomes a bioreactor to produce biodiesel from generic biomass. In effect, the algae in oil-production sub-system 10 becomes a conversion vehicle which converts feed sugar formed from generic biomass into algal oil which can then be converted to biodiesel as described below.

A feed biomass source, whether algal biomass 26, non-algal biomass 24, or a combination of the two, can be operatively connected to a depolymerizing reactor 32. The reactor can be configured for forming sugars from the feed biomass source by providing suitable operating conditions. In the present invention, one approach is to use biological enzymes to depolymerize (break down) the biomass into sugars or other simple molecular structures which can be used as feed for the oil-producing algae.

A feed separator 34 can be operatively connected to the depolymerizing reactor and the algae growth reservoirs. The feed separator can direct at least a portion of the algal feed to the algae growth reservoirs 6 as a feed for the dark or heterotrophic stage of the oil-producing algae in cultivation sub-system 10. The remainder of the algal feed can be sent forward to a fermentation sub-system 40 to form ethanol and/or ethyl acetate, or alternatively other alcohols.

Fermentation

The fermentation stage can be conventional in its use of yeast to ferment sugar to alcohol. The fermentation process produces carbon dioxide, alcohol, and algal husks. All of these products can be used elsewhere in the process and systems of the present invention, with substantially no unused material or wasted heat. Alternatively, if ethanol is so produced, it can be sold as a product or used to produce ethyl acetate for the transesterification process. Similar considerations would apply to alcohols other than ethanol.

A fermentation sub-system 40 for forming ethanol and/or ethyl acetate can include a fermentation reactor operatively connected to a sugar separator of the feed sub-system 30. The fermentation reactor can be configured for production of ethanol 36 and/or ethyl acetate 38. In one preferred aspect, both ethanol and ethyl acetate can be formed using separate fermentation reactors. For example, ethanol can be formed in a first reactor 37 and at least a portion of the ethanol can be reacted with acetic acid from a second reactor 36 to form ethyl acetate in a third reactor 38. The ethyl acetate can generally be formed in the presence of other compounds and components such as, but not necessarily included with or limited to, water, ethanol, acetic acid, etc. A fermentation separator can be operatively connected to the fermentation reactor for separating $CO_2$ product 46, ethanol and/or ethyl acetate 44, and biomass residues 42.

The carbon dioxide 46 can be captured and returned to either the light 2 or dark stage 6 of the oil-producing algae cultivation step as a carbon source to increase production of oil. A suitable $CO_2$ recycle line or other system can be used to direct the carbon dioxide accordingly. Biomass and/or algal residues 42 can be burned 62 from the steps of fermenting and extracting an algal oil to produce heat which can be distributed to any portion of the process as required, e.g. warming of algae reservoirs, and other process heat. At least a portion of ethanol or ethyl acetate product 44 can be used in the conversion of the algal oil to biodiesel via transesterification sub-system 50. Any excess ethanol 48 can be stored after distillation and sold as bioethanol. If other alcohols, e.g. butanol, are produced rather than ethanol, the fermentation sub-system 40 would be adjusted accordingly.

Conversion of Algal Oil to Biodiesel

Algal oil can be converted to biodiesel through a process of direct hydrogenation or transesterification of the algal oil.

Algal oil is in a similar form as most vegetable oils, which are in the form of triglycerides. A triglyceride consists of three fatty acid chains, one attached to each of the three carbon atoms in a glycerol backbone. This form of oil can be burned directly. However, the properties of the oil in this form are not ideal for use in a diesel engine, and without modification, the engine will soon run poorly or fail. In accordance with the present invention, the triglyceride is converted into biodiesel, which is similar to but superior to petroleum diesel fuel in many respects.

One process for converting the triglyceride to biodiesel is transesterification, and includes reacting the triglyceride with alcohol or other acyl acceptor to produce free fatty acid esters and glycerol. The free fatty acids are in the form of fatty acid alkyl esters (FAAE).

A transesterification reactor 52 of transesterification subsystem 50 can be operatively connected to the oil extraction bioreactor of extraction sub-system 20 to convert at least a portion of the algal oil to biodiesel. Transesterification can be done in several ways, including biologically and/or chemically. The biological process uses an enzyme known as a lipase 54 to catalyze the transesterification, while the chemical process uses a synthetic catalyst 54 which may be either an acid or a base. The lipase-catalyzed reaction is preferable because it involves no harsh chemicals and produces a high-quality product in the simplest way. Further, the use of ethyl acetate can be preferred over ethanol or other alcohol in transesterification since alcohol can be excessively damaging to enzyme activity. As such, in one embodiment of the present invention, transesterifying can include introducing an enzyme for converting the algal oil to biodiesel. Non-limiting examples of suitable lipase may include, but are not limited to, those from *Rhizomucor miehei*, *Thermomyces lanuginose*, *Pseudomonas fragi*, and *Candida cylindracea*, and those described in U.S. Pat. Nos. 4,472,503 and 5,316,927, which patents are incorporated herein by reference.

With the chemical process, additional steps are needed to separate the catalyst and clean the fatty acids. In addition, if ethanol is used as the acyl acceptor, it must be essentially dry to prevent production of soap via saponification in the process, and the glycerol must be purified. The biological process, by comparison, can accept ethanol in a less dry state and the cleaning and purification of the biodiesel and glycerol are much easier. Either or both of the biological and chemically-catalyzed approaches can be useful in connection with the processes of the present invention.

Transesterification often uses a simple alcohol, typically methanol derived from petroleum. When methanol is used the resultant biodiesel is called fatty acid methyl ester (FAME) and most biodiesel sold today, especially in Europe, is FAME. However, ethanol can also be used as the alcohol in transesterification, in which case the biodiesel is fatty acid ethyl ester (FAEE). In the U.S., the two types are usually not distinguished, and are collectively known as fatty acid alkyl esters (FAAE), which as a generic term can apply regardless of the acyl acceptor used. Direct hydrogenation can also be utilized to convert at least a portion of the algal oil to a biodiesel. As such, in one aspect, the biodiesel product can include an alkane.

The process of the present invention focuses on the use of ethanol or ethyl acetate for transesterification because both substances can be readily produced as part of the fermentation sub-system 40 rather than from external sources. This further lowers cost because the ethanol or ethyl acetate can be derived from plant material rather than from fossil sources. The ethanol may be used directly as the alcohol or may be converted first to ethyl acetate to extend the longevity of the lipase enzyme, if used.

Glycerol produced in transesterification 60 may be used as a drying agent to dry the ethanol 56 for transesterification, and may also be sold 60 as a product. To be used as a drying agent, the glycerol can be first purified and dried. Pure dry glycerol is a chemical drying agent because it attracts and holds water. The ethanol produced from the fermentation described above is preferably essentially dry (anhydrous) to be used in chemical transesterification. Ethanol can only be dried to approximately 96% by distillation because at this point the alcohol forms an azeotrope with water and the two components cannot be separated further by conventional distillation. Thus, a distillation device can be operatively connected between the fermentation separator and the transesterification reactor. The remaining water can be removed chemically, and the dry glycerol produced from transesterification can be used as the drying agent.

The algal triglyceride can also be converted to biodiesel by direct hydrogenation. In this process, the products are alkane chains, propane, and water. The glycerol backbone is hydrogenated to propane, so there is substantially no glycerol produced as a byproduct. Furthermore, no alcohol or transesterification catalysts are needed. All of the biomass can be used as feed for the oil-producing algae with none needed for fermentation to produce alcohol for transesterification. The resulting alkanes are pure hydrocarbons, with no oxygen, so the biodiesel produced in this way has a slightly higher energy content than the alkyl esters, degrades more slowly, does not attract water, and has other desirable chemical properties.

Final Products

The final products from the processes presented herein are large amounts or proportions of biodiesel 58 and possibly lesser amounts or proportions of bioethanol 48 resulting from any excess production not used for biodiesel. If direct hydrogenation is used, then no alcohol will be produced. If transesterification is used, glycerol is produced and may be sold as a byproduct.

In addition, the process of the present invention can be highly efficient and energy-positive, meaning the energy produced in the form of fuels is far in excess of external input energy, because very little fossil energy is used. Algae growth requires none of the heavy machinery, expensive fuels, or chemical fertilizers and pesticides required by conventional agriculture. Further, the algae can be processed near the growth ponds, eliminating transportation costs.

Comparison of Biodiesel to Petroleum Diesel

Following is a discussion of some of the qualities and advantages of biodiesel compared to petroleum diesel. Biodiesel formed in accordance with the present invention is atmospherically carbon-neutral. In other words, substantially all carbon released in combustion and/or fermentation was previously removed from the atmosphere during growth. Algal oil contains little or no sulfur, so production of biodiesel using the present invention reduces sulfur emissions, even compared to ultra low sulfur petroleum diesel. Because of better combustion efficiency, biodiesel produces about 20% less carbon monoxide upon use by a consumer. Biodiesel burns more efficiently which results in a smoother-miming engine. The equivalent cetane number of biodiesel is higher than petroleum diesel, reducing diesel noise and knock. Biodiesel produces less soot, reducing particulate emissions by up to 75% and nearly eliminating the black smoke often associated with diesel engine exhausts. The alkyl esters or alkanes in biodiesel contain chains with none of the ring structures found in petroleum diesel. These petroleum ring structures or aromatic hydrocarbons give diesel fuel and diesel exhaust its characteristic smell. The smell of biodiesel fuel and biodiesel exhaust is cleaner and lacks most of the familiar diesel aroma. Biodiesel also has a higher flash point near 150° C. compared to petroleum diesel at 70° C., so it is safer to store and handle. Biodiesel breaks down about four times faster in the environment, so spills are less enduring. Biodiesel has higher lubricity so fuel injection systems and other engine components can have a longer life. Further, biodiesel can be mixed with petroleum diesels during the transition to 100% biodiesel fuels. Importantly, conventional diesel engines do not need to be modified to use biodiesel.

Although superior in many respects, several factors can also be considered when using biodiesel. FAME (methyl ester) produces slightly less power in a diesel engine (app. 5% less) than petroleum diesel. However, since the engine runs smoother when combusting biodiesel this drop in power is rarely noticed. Because alkyl esters break down faster, it cannot be stored as long as petroleum diesel or it may degrade, though this problem does not exist with alkanes produced by hydrogenation. Biodiesel is a solvent which increases solubility of many materials over petroleum diesel. As a result, older fuel tanks and systems may release accumulated rust or sludge until the fuel system is cleaned out.

Between FAEE and FAME, FAEE can be preferred for several reasons. The extra carbon in ethyl ester compared to methyl ester increases the heat content of the fuel, improving mileage and making the fuel comparable to petroleum diesel. The cetane number of ethyl ester is also higher, making the fuel burn more smoothly than methyl ester. Ethyl ester has higher flash and combustion points, making it safer to store and use. Ethyl ester produces even less black smoke and has a lower exhaust temperature than the methyl ester variant.

It is to be understood that the above-referenced arrangements are illustrative of the application for the principles of the present invention. Numerous modifications and alternative arrangements can be devised without departing from the spirit and scope of integrated process and systems of the present invention. While the present invention has been shown in the drawings and described above in connection with the exemplary embodiments(s) of the invention, it will be apparent to those of ordinary skill in the art that numerous modifications can be made without departing from the principles and concepts of the invention as set forth in the claims.

What is claimed is:

1. A process for production of biofuels from algae, comprising:
    a) cultivating an oil-producing algae by photoautotrophic growth;
    b) producing algal oil by heterotrophic growth of the oil-producing algae wherein the heterotrophic growth is fed by introducing a sugar feed to the oil-producing algae; and
    c) extracting an algal oil from the oil-producing algae.

2. The method of claim 1, further comprising converting the oil to biodiesel.

3. The process of claim 1, wherein the oil-producing algae includes a member selected from the group consisting of diatoms (bacillariophytes), green algae (chlorophytes), blue-green algae (cyanophytes), golden-brown algae (chrysophytes), haptophytes, and combinations thereof.

4. The process of claim 3, wherein the oil-producing algae includes *Amphipleura, Amphora, Chaetoceros, Cyclotella, Cymbella, Fragilaria, Hantzschia, Navicula, Nitzschia, Phaeodactylum, Thalassiosira, Ankistrodesmus, Botryococcus, Chlorella, Chlorococcum, Dunaliella, Monoraphidium, Oocystis, Scenedesmus, Tetraselmis, Oscillatoria, Synechoccus, Boekelovia*, or combinations thereof.

5. The process of claim 4, wherein the oil-producing algae includes *Chlorella, Dunaliella*, or combinations thereof.

6. The process of claim 1, further comprising introducing a nitrogen-fixing algae to the oil-producing algae to provide nitrogen as a nutrient.

7. The process of claim 6, wherein the oil-producing algae is the nitrogen-fixing algae.

8. The process of claim 6, wherein the nitrogen-fixing algae includes blue-green algae or cyanobacteria.

9. The process of claim 1, wherein the sugar feed is the primary source of both carbon and energy in the heterotrophic growth stage.

10. The process of claim 1, wherein introducing the sugar feed further includes cultivating algae and extracting the sugar feed therefrom.

11. The process of claim 1, wherein the heterotrophic growth stage is initiated using a stress induction mechanism.

12. The process of claim 11, wherein the stress induction mechanism includes at least one of light deprivation, nutrient deprivation, injection of a reactive oxygen source, a lipid trigger, and chemical additives.

13. The process of claim 1, wherein the photoautotrophic growth stage and the heterotrophic growth stage overlap in time.

14. The process of claim 1, wherein the photoautotrophic growth stage and the heterotrophic growth stage are performed substantially simultaneously.

* * * * *

UNITED STATES PATENT AND TRADEMARK OFFICE
CERTIFICATE OF CORRECTION

PATENT NO. : 8,475,543 B2
APPLICATION NO. : 13/026767
DATED : July 2, 2013
INVENTOR(S) : James R. Oyler It is certified that error appears in the above-identified patent and that said Letters Patent is hereby corrected as shown below:

In the Specification

Column 1; line 12, Add:

--GOVERNMENT INTEREST

This invention was made with government support under Grant Number DE-EE0003046 awarded by the Department of Energy. The Government has certain rights to this invention.--

Signed and Sealed this
Thirtieth Day of June, 2015

Michelle K. Lee
*Director of the United States Patent and Trademark Office*